(12) United States Patent
Janke et al.

(10) Patent No.: US 6,420,465 B1
(45) Date of Patent: Jul. 16, 2002

(54) PROCESS FOR PREPARING PHOSPHORIC ACID ESTERS

(75) Inventors: Nikolaus Janke, Dormagen; Reinhard Pech, Haan; Andreas Chrisochoou, Köln; Dieter Heinz, Leverkusen; Werner Bäcker, Wipperfürth; Kaspar Hallenberger, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/729,021

(22) Filed: Dec. 4, 2000

(30) Foreign Application Priority Data

Oct. 16, 2000 (DE) .......................................... 100 51 119

(51) Int. Cl.$^7$ .............................. C08K 5/52; C07K 9/09
(52) U.S. Cl. .......................................... 524/126; 558/92
(58) Field of Search ........................... 524/126; 558/92, 558/110

(56) References Cited

U.S. PATENT DOCUMENTS

| 5,281,741 A | 1/1994 | Gunkel et al. ................. 558/92 |
| 5,958,511 A | 9/1999 | Dolan ......................... 427/258 |
| 6,124,492 A | 9/2000 | Su et al. ...................... 558/100 |

FOREIGN PATENT DOCUMENTS

| EP | 0 936 243 | 8/1999 |
| JP | 10-7689 | 1/1998 |
| JP | 10-17583 | 1/1998 |
| WO | 97/47631 | 12/1997 |
| WO | 98/35970 | 8/1998 |
| WO | 99/55771 | 11/1999 |

*Primary Examiner*—Deborah C. Lambkin
(74) *Attorney, Agent, or Firm*—Joseph C. Gil; Diderico van Eyl

(57) ABSTRACT

The present invention relates to a process for preparing phosphoric acid esters, in particular monomeric bisaryl diphosphates, or bridged phosphates.

14 Claims, No Drawings

PROCESS FOR PREPARING PHOSPHORIC ACID ESTERS

The present invention relates to a process for preparing phosphoric acid esters, in particular a continuous process for preparing monomeric bisaryl diphosphates, or bridged phosphates.

Bisaryl diphosphates, such as bisphenol A bis(diphenyl) phosphate and resorcinol bis(diphenyl)phosphate are known to be effective flame retardants for polymer resins. For example, a variety of polyphenylene oxide/high-impact polystyrene ("PPO/HIPS") and polycarbonate/acrylonitrile-butadiene-styrene ("PC/ABS") blends can be improved with bisaryl diphosphate flame retardants.

When using bisaryl diphosphates to impart flame retardancy to plastics it is desired to use compounds having a high percentage of the monomer. This is because monomeric bisaryl diphosphates impart beneficial physical properties to the polymer, which properties are not provided by their dimeric or polymeric counterparts. For example, resins to which monomeric bisaryl diphosphates have been added exhibit improved impact strength, melt flow index, tensile properties and flexural properties when compared to resins combined with dimeric or polymeric aryl phosphates.

Because of their commercial utility, various processes for the manufacture of monomeric bisaryl diphosphates have been developed. For example, it is known that bisphenol-A bis(diphenyl)phosphate can be obtained by catalytically reacting a phosphorus oxyhalide with bisphenol A (BPA) and then reacting the intermediate with phenol.

WO 99/55771 describes a process for continuously preparing monomeric bisaryl diphosphates, which, however, are not worked up and thus do not meet all requirements of a flame retardant for polymer resins with regard to certain product properties (catalyst content, acid number, hydrolysable chlorine).

It is known from EP 936243 A2 that acid components and/or precursors thereof which, under conditions of heat and humidity, lead to the formation of acid components, are typically present in the bisaryl diphosphates. These impurities may originate from, for example, catalyst residues, unreacted starting materials, such as phosphoryl halides and/or phosphoric acid ester derivatives, or from decomposition products of unstable phosphoric acid esters. It has also been found that such impurities as flame retardant additives in polymer resins compromise the hydrolytic stability.

WO 98/47631 discloses a process for preparing aryl diphosphate esters, which comprises a third stage of filtering off the catalyst which is unsoluble in the reaction medium.

WO 98/35970 describes a semicontinuous process for preparing bisaryl diphosphates using magnesium chloride as a catalyst. The reaction product is not worked up here either.

EP 0485 807 B1 describes a process for preparing aryl diphosphate esters in eight process steps, a workup or extraction of the catalyst being carried out in aqueous alkaline solution.

JP-A 10/017 583 dicloses a batchwise synthesis for preparing phosphate ester oligomers, the reaction being controlled via the liberation rate of HCl gas. Excess phenol is removed by distillation, whereas the catalyst, for example magnesium chloride, is removed by washing.

Finally, JP-A 10/00 7689 discloses a process for removing the metal chloride catalyst by means of an acidic aqueous solution (pH$\leq$3) and at a temperature of at least 65° C.

A disadvantage of the prior art preparation processes is that, in the absence of a workup procedure, the desired products can be obtained only in a form contaminated with catalyst and other acidic minor components, or that, in the case of bridged aryl phosphates, in particular the reaction products of bisphenol A or resorcinol, the workup or washing prodecures suggested lead to considerable difficulties in largescale plants owing to the poor phase separation between the product phase and the water phase and to the strong hydrolysis tendency in particular in alkaline media. At present, these difficulties prevent the realization of a continuous and thus industrialscale production of these products.

The present invention therefore provides a process for preparing phosphoric acid esters, in particular monomeric bisaryl diphosphates or bridged phosphates, characterized in that (1) a phosphorus oxyhalide is reacted continuously, semicontinuously or batchwise with a polyol to produce a content of at least about 60% monomeric halophosphate intermediate, (2) the monomeric halophosphate intermediate is reacted continuously, semicontinuously or batchwise with an alcohol to produce the desired phosphoric acid ester, and (3) the product from Step 2 is worked up continuously, semicontinuously or batchwise in a phase separator at temperatures of 50 to 120° C.

In some preferred embodiments, the polyol in Step 1 is a dihydric alcohol and the alcohol in Step 2 is a monohydric alcohol. Conversely, in some preferred embodiments the phosphorus oxyhalide is reacted with a monohydric alcohol to produce a content of at least about 60% monohalomonophosphoric acid diester intermediate. In a preferred embodiment, all three steps are carried out continuously.

It is an object of the present invention to provide a method for continuously producing phosphoric acid esters, wherein at least one step is carried out continuously. Particularly preferably all three steps are carried out continuously.

Another object of the present invention is to provide a method for producing phosphoric acid esters in a continuous reaction, wherein the monomeric halophosphate intermediate content of a reaction between phosphorus oxyhalide and a polyol is at least about 60%, preferably at least about 70% and particularly preferably at least about 80%.

A further object of the invention is to provide a method for producing monomeric phosphoric acid ester products which can be used as flame retardants, for example, in plastics.

Further objects and advantages of the present invention will be apparent from the following description.

The term continuous as used herein means that the reactants are fed into the apparatus at a constant flow rate and the reaction mixture is removed in an equally continuous manner. All reaction parameters are kept constant over time.

The term semicontinuous as used herein means that one reactant is introduced into the apparatus whereas another reactant is added slowly and continuously.

The term batchwise or discontinuously as used herein means that the reactants are introduced together into the apparatus, where they remain for a defined reaction time under set reaction conditions.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications in the illustrated methods, and such further applications of the principles of the invention as illustrated therein, being contemplated as would normally occur to one skilled in the art to which the invention relates.

Preferably, the present invention relates generally to a continuous process for producing phosphoric acid esters, wherein all three steps are run continuously, so that a product can be produced which has a high monomeric halophosphate intermediate content relative to dimeric halophosphate intermediate content, along with high productivity, when the reaction is carried out in a continuous reactor system, such as a continuous stirred tank reactor (CSTR). The intermediate can be used, in certain embodiments, to form a desired monomeric phosphoric acid ester, including BPA bis(diphenyl)phosphate.

The preferred reactor design (i.e., a continuous reactor) allows the production of product ratios otherwise unattainable in commercial quantities at high productivity.

The degree of oligomerization or polymerization can further be controlled to some extent by the degree of reaction completion in individual stages of a multiple stage continuous reactor series.

In one aspect of the invention, phosphoric acid esters are continuously produced by a two step process. In the first step, a content of at least about 60% monomeric halophosphate intermediate, preferably a bis(dichlorophosphate), is formed by continuously reacting a phosphorus oxyhalide with an alcohol, preferably a diol or other polyol. After preferably removing the excess phosphorus oxyhalide, the monomeric halophosphate intermediate is reacted with another alcohol, preferably a monohydric alcohol such as a phenol, to produce a desired phosphoric acid ester. The phosphorus oxyhalide, which has been removed for example by distillation, can be returned to the process, i.e. re-used for preparing the halophosphate intermediate.

The products of the Step 1 reaction are predominantly monomeric, and, as the monomeric product is used as a reactant in Step 2, the product of the Step 2 reaction will likewise be predominantly monomeric. However, it is recognized that, should one desire an oligomeric or polymeric component after forming the monomeric product from Step 1, the monomeric product from Step 1 may be reacted with a polyol in Step 2 and the resultant product may be farther processed as desired.

In yet another aspect of the invention, the desired phosphoric acid esters are produced by continuously reacting phosphorous oxyhalide with a monohydric alcohol to produce a content of at least about 60% monohalomonophosphoric acid diester intermediate. The intermediate is then reacted with a polyol, preferably a dihydric alcohol, to produce the desired phosphoric acid ester.

Further describing one embodiment of the processes of the present invention, Step 1 of a process for preparing phosphoric acid esters preferably includes continuously reacting an appropriate alcohol with phosphorus oxyhalide in the presence of a Lewis acid catalyst. The phosphorus oxyhalide used in the present invention is generally of the formula $POX_n$ where X is a halide, including chloride or bromide, and n is preferably 3. Phosphorus oxychloride, $POCl_3$, is the most preferred phosphorus oxyhalide.

Step 1 produces a monomeric halophosphate intermediate when a polyhydric alcohol, such as a dihydric alcohol, is used. In that embodiment, the Step 1 reaction proceeds, diagrammatically, as follows:

Any unreacted $POX_3$ is removed by distillation under reduced pressure, leaving the Step 1 intermediate product I.

In the above diagram, R is the carbon chain portion (i.e. the aromatic, aliphatic, alicyclic portion or a combination thereof) of the alcohol, X is a halide as previously mentioned and compound I is the monomeric halophosphate intermediate product of Step 1.

Examples of appropriate alcohols include polyols, such as polyphenols, and including dihydric alcohols such as biphenols, bisphenol A, tetrabromobisphenol A, bisphenol S, bisphenol F, ethylene glycol, 1,4-butanediol, 1,2-hexanediol, resorcinol, catechol, hydroquinone and trihydric alcohols such as glycerol as well as other polyols. The aromatic and alicyclic portions of the alcohols may be alkyl- or halo-substituted. The aliphatic portion of the alcohol may also be halo-substituted. The alkyl substituent comprises saturated or unsaturated aliphatic hydrocarbon groups which may be either straight-chain or branched and have a carbon chain length of from 1 to 18. For example, the alkyl group includes methyl, ethyl and structural isomers of propyl, butyl, pentyl, hexyl, heptyl, octyl, nonyl, decyl, undecyl, dodecyl, tridecyl, tetradecyl, pentadecyl, hexadecyl, heptadecyl and octadecyl. The halo substituent is preferably chlorine and/or bromine. It is further preferred that there is no more than one substituent ortho to each hydroxyl group on an aromatic alcohol.

The catalyst may be any Lewis acid capable of promoting the reaction. Examples include, but are not limited to, $AlCl_3$, $ZnCl_2$, $CaCl_2$, $MgO$ or $MgCl_2$, preferably $MgO$ or $MgCl_2$. The catalyst is used in an amount sufficient to allow the reaction to proceed smoothly. The amount of catalyst used in Step 1 is typically in the range of about 100 ppm to about 5000 ppm (relative to the other reagents added to the first reactor), preferably 100 ppm to about 1000 ppm and most preferably about 300 ppm to about 700 ppm.

The reaction temperature in Step 1 will depend on the specific polyol reacted, but generally can be controlled over a wide range, from about 50° C. to about 250° C., and the process may be operated at atmospheric pressure, at a reduced pressure, or at an elevated pressure. However, a temperature of about 50° C. to about 200° C. is preferred, a temperature of about 80° C. to about 140° C. is particularly preferred, and a temperature of about 85° C. to about 100° C. in the first stage and second stage and about 100° C. to about 120° C. in subsequent stages is most preferred.

In the first step, the process may be operated with a sufficient excess of $POX_3$ to yield a workable reaction mass at the reaction temperature, or an unreactive solvent may be used. The phosphorus oxyhalide/polyol mole ratio is typically about 2.5:1 to about 10:1, preferably about 3:1 to about 6:1 and most preferably about 4:1 to about 5:1. The residence time in each reactor may vary from 0.25 hours to about 6 hours.

As mentioned above, the degree of oligomerization or polymerization can further be controlled to some extent by the degree of reaction completion in individual stages of a multiple stage continuous reactor series. The degree of reaction completion in Stage 1 of Step 1 is typically about 10 to about 100%, and about 20% to about 100% in subsequent stages. However, it is preferred that the degree of reaction completion in Stage 1 be about 30% to about 80% and in subsequent stages about 50% to about 100%. It is most preferred that the degree of reaction completion in Stage 1 be about 30% to about 50%, in Stage 2 about 70% to about 100% and in subsequent stages about 85% to about 100%.

The reaction of Step 1 is carried out by continuous, semicontinuous or batchwise, preferably continuous reaction of the above-described reagents. As used herein, the term "continuously reacting" means that at least one step, such as Step 1 or 2 or 3, can be carried out at least partly continuously (i.e. the step can be divided into various stages and at least one stage is carried out continuously) or the entire step can be carried out continuously. The number of stages may range from about 1 to about 5, preferably from about 1 to about 3 and most preferably from about 2 to about 3.

However, it is also possible to carry out Step 1 and Step 2 in continuous or semicontinuous mode and only Step 3 in batchwise mode. Alternatively, it is also possible to carry out only Step 2 and Step 3 in continuous or semicontinuous mode and only Step 1 in batchwise mode.

It is likewise possible to use any combination of continuous, semicontinuous or batchwise operation of the individual steps, including batchwise operation of all Steps 1, 2 and 3.

The term "continuous reactor" as used herein refers to a vessel where raw materials or a feed stream containing unreacted or partially reacted material is added continuously or essentially continuously while material is being removed from the vessel to maintain an essentially constant reactor volume, and where conditions in the vessel are such that a finite degree of reaction occurs.

As indicated above, the selection of reactor design to accomplish the continuous portion of the reaction in either Step 1 or Step 2 or Step 3 plays an important role in determining the degree of oligomerization or polymerization and the quality of the product. Examples of commercially available reactors that might be used to practice the invention, and that one skilled in the art is familiar with, include falling film or thin film reactors, continuously stirred tank reactors (CSTRs), tube reactors and packed column reactors. Although a wide variety of reactors may be used to practice the invention, CSTRs are preferred.

A series of continuous reactors may employ the same type, or a different type, of reactor. It is further preferred that a CSTR be used in Stage 1 of a step and then either another CSTR may be used or a batch reactor may be used. It is most preferred to use a series of CSTRs or, alternatively, a series of CSTRs, the final stage being carried out in a batch reactor.

It is noted that, along with the monomeric product produced in the Step 1 reaction diagrammed above, dimeric, other oligomeric or polymeric products may be formed. For example, referring to the diagram of the Step 1 reaction above, compound 1 may react with Step 1 reactants (i.e., with the dihydric alcohol and $POX_3$) to form the following dimeric component:

The above dimeric component may also be produced by reaction of the following reactants and intermediates from the reaction of Step 1:

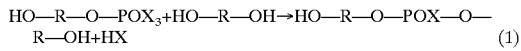 (1)

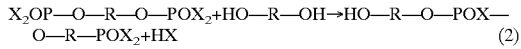 (2)

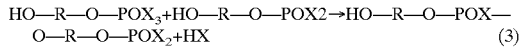 (3)

It is obvious that the product formed from (1)–(3) above must be further reacted with $POX_3$ to form the dimeric component.

A suitable methode for determining the relative amounts of monomer, dimer and futher homologues of Step 1 is liquid chromatography (GPC) using an RI detector.

The reaction of Step 1 preferably forms a content of at least about 60% monomeric halophosphate intermediate. It is further preferred that the reaction of Step 1 forms a content of at least about 70%, particularly preferably at least about 80%, monomeric halophosphate intermediate.

Referring now to Step 2 of the process, the product of Step 1 is reacted with an alcohol, such as a monohydric alcohol including phenol, in a similar way using a Lewis acid catalyst. In one embodiment, Step 2 may be depicted diagrammatically as follows:

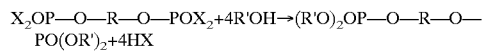

X and R are as defined above for Step 1 and $X_2OP$—O—R—O—$POX_2$ is a monomeric halophosphate intermediate. R'OH is the monohydric alcohol, R' being the carbon chain portion (i.e., the aromatic, aliphatic, alicyclic, portion or a combination thereof) of the alcohol, and $(R'O)_2OP$—O—R—O—$PO(OR')_2$ is the desired phosphoric acid ester product. When R'OH includes an aromatic or alicyclic ring, the aromatic or alicyclic ring may be alkyl- or halo-substituted as discussed above for the dihydric alcohol in Step 1. The aliphatic portion of the alcohol may also be halo-substituted as discussed above. It is further preferred that there is no more than one substituent ortho to each hydroxyl group on an aromatic alcohol. Examples of the alcohol that may be reacted in Step 2 include, but are not limited to, phenol, xylenols, tribromophenol, methanol, t-butanol, cyclohexanol and phenol/formaldehyde condensates. It is preferred to carry out Step 2 by reacting the halophosphate intermediate product of Step 1 with phenol using magnesium chloride as a catalyst.

As in the first step, the phenol (or other alcohol) and the product of Step 1 can be continuously fed to a CSTR in Step 2. Alternatively, the phenol (or other alcohol) can be added as a single charge to the product of Step 1, and the resulting mixture can be fed continuously to the reactor.

The discharge from the first continuous reactor may be fed to a second continuous reactor where the material is held at 125-250° C. for a residence time of about 0.25–6 hours. The total phenol charge may be added to the first reactor or split such that part of the total phenol charge is added to the first reactor and the remainder added to the second reactor.

The discharge from the second reactor is fed to a buffer tank. The buffer tank is used to feed a continuous or batch vacuum stripper adapted to remove excess alcohol from Step 2, such as phenol. The alcohol, for example phenol, excess which has been removed can be returned to the process, i.e. reused for carrying out Step 2. A catalyst is used as in the reaction of Step 1.

The reaction of Step 2 is typically performed at a temperature sufficient to convert the halophosphate intermediate to the desired phosphoric acid ester product. Although this temperature may vary depending on the reagents used and the desired product, the temperature of the material in the reactor advantageously ranges from 50° C. to about 250° C., but preferably from about 125° C. to about 250° C. The volume of the reactor is preferably adjusted so that the residence time ranges from about 0.25 to 6 hours.

The alcohol/monomeric halophosphate intermediate mole ratio is typically about 4:1 to about 5:1, but preferably about 4.04:1 to about 4.40:1, and most preferably about 4.04:1 to about 4.12:1. As in the first step, an excess of the alcohol may be used to improve the ease of processing, or an unreactive solvent may be employed.

In a preferred embodiment of the first aspect of the invention, BPA is continuously added to magnesium chloride and phosphorus oxychloride in a dissolution vessel at a temperature of about 50° C. The relative feed rates are such that the phosphorous oxychloride/BPA mole ratio is about 5:1. The reaction mixture is then fed to a first CSTR at a temperature of about 90° C. The volume of the reactor is maintained to give a residence time of about 1 hour.

The contents of the first reactor are continuously removed and transferred to further CSTRs arranged in series, successively increasing the temperature to about 100° C. and finally 120° C. The feed and discharge rates from the reactor are such that the residence time is about 1 hour in each case.

The discharge from the last reactor is fed to a buffer tank, which is maintained at about 90° C. while being filled. The filled buffer tank is used to feed a continuous distillation to remove the excess $POCl_3$ from the product of Step 1.

The product of Step 1 is then reacted with phenol using magnesium chloride as a catalyst.

As briefly mentioned above, the inventive continuous process may be operated such that part of the first step or second step is performed in a continuous reactor with the rest of the reaction being completed in a batchwise reactor or reactors. Similarly, an entire step may be performed in a continuous reactor or series of continuous reactors, while the other step is carried out in batch reactors. The steps may be carried out so as to maximize production of monomeric halophosphate intermediate product and, consequently, monomeric phosphoric acid ester product.

The monomer content of the reaction product of Step 2 depends on the presence of a high percentage of monomeric halophosphate intermediate which acts as a reactant in Step 2. Thus, if a large amount of monomeric halophosphate intermediate is produced in Step 1 relative to the dimeric component, the monomer content of the reaction of Step 2 will also be relatively large. That is, relatively large amounts of the monomeric phosphoric acid ester product of Step 2 will be formed compared to dimeric, oligomeric or polymeric phosphoric acid ester product.

Parameters that can affect the properties and quality of the products of Step 1 and Step 2 include catalyst selection and amount of catalyst used, and phosphorus oxyhalide/alcohol ratio. Each of these parameters has an optimum range to give a flame retardant material exhibiting the desired properties. In addition, the moisture content of each starting material has an effect on the final product quality. For example, if the moisture content of the reactants is kept low, a larger amount of monomeric product can be obtained.

When Step 1 or Step 2 are performed in a series of reactors, at least one of which is a continuous reactor, the raw materials, such as solvent, catalyst, phosphorus oxyhalide, alcohol (i.e. phenol or polyol, such as a diol) may be added to just the first reactor in the series or to downstream reactors in addition to the first. This can be done to improve the ease of processing, to control product quality and/or to obtain the desired product or mixture of products.

In an alternative embodiment, a process for preparing phosphoric acid esters is provided which is characterized in that (1) a phosphorus oxyhalide is reacted continuously, semicontinuously or batchwise with a monohydric alcohol to produce a content of at least about 60% monohalomonophosphoric acid diester intermediate, (2) said monohalomonophosphoric acid diester intermediate is reacted continuously, semicontinuously or batchwise with a polyol to produce the desired phosphoric acid ester, (3) the product from Step 2 is worked up continuously, semicontinuously or batchwise in a phase separator at temperatures of 50 to 120° C., preferably 70 to 90° C.

In this second aspect of the invention, the products from this step are then reacted with the chosen alcohol selected from the alcohols described above, preferably a polyol, such as a diol, to give the desired phosphoric acid ester. This route also utilizes Lewis acid catalysts and continuous addition of reactants as described for the other embodiments. Step 2 product composition and properties are similar to those obtained in the previously described route. The inventive continuous process may be operated in a similar fashion as described above. For example, in certain embodiments the reaction of the intermediate with the polyol may also be performed in a continuous reactor. Alternatively, the first reaction may be performed in a batch reactor and the second reaction may be performed continuously.

Referring more specifically to the above alternative embodiment, the Step 1 reaction of the monohydric alcohol with the phosphorus oxyhalide may be diagrammed as follows:

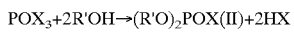

$$POX_3 + 2R'OH \rightarrow (R'O)_2POX(II) + 2HX$$

R'OH and X are as previously defined and compound II is the monohalomonophosphoric acid diester intermediate.

The specific catalyst and the quantity used are the same as in the previous embodiments discussed.

The reaction temperature in Step 1 of the alternative embodiment can likewise be controlled over a wide range, from about 50° C. to about 250° C., and the process may similarly be operated under various pressures. However, a temperature of 50° C. to about 200° C. is preferred, and a temperature of about 90° C. to about 140° C. is particularly preferred. Moreover, residence times are typically about 0.25 hours to about 6 hours.

The alcohol/phosphorus oxyhalide mole ratio is advantageously from about 1.5:1 to about 3:1, and particularly preferably from about 1.75:1 to about 2.25:1.

Reaction of phosphorus oxyhalide with a monohydric alcohol may yield the following undesired compounds:

$$(R'O)POX_2 (III)$$

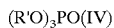

$$(R'O)_3PO(IV)$$

Compound III is a dihalomonophosphoric acid monoester intermediate and Compound IV is a phosphoric acid triester. Compound IV is undesired as this compound can no longer react with a polyol in Step 2 to produce a desired phosphoric acid ester product. Compound III is undesired because it has the potential of reacting with the reactants and intermediates formed in the reaction of Step 2, and can thus lead to formation of dimeric, oligomeric or polymeric products in Step 2. As one skilled in the art is aware of the specific undesired reactions that may proceed and products that may be produced, it is not necessary to describe them here.

The reaction between phosphorus oxyhalide and the monohydric alcohol will typically produce a content of at least about 60% monohalomonophosphoric acid diester. It is further preferred that at least about 70%, particularly preferably at least about 80%, of the monohalomonophosphate diester is produced.

Step 2 of the alternative embodiment may be diagrammed as follows:

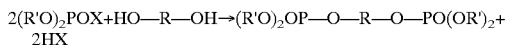

$$2(R'O)_2POX + HO-R-OH \rightarrow (R'O)_2OP-O-R-O-PO(OR')_2 + 2HX$$

R' and X are as defined above. The reaction of Step 2 produces the desired monomeric phosphoric acid ester product, $(R'O)_2OP-O-R-O-PO(OR')_2$.

The specific catalyst and the quantity used is the same as in the embodiments discussed previously.

The reaction temperature in Step 2 of the alternative embodiment can also be controlled over a wide range, from about 50° C. to about 250° C., and the process may similarly be operated under various pressures. However, a temperature of about 125° C. to about 250° C. is preferred. Moreover, residence times are typically about 0.25 hours to about 6 hours.

The polyol/monohalomonophosphoric diester intermediate mole ratio is advantageously from about 0.3:1 to about 0.8:1, and particularly preferably from about 0.4:1 to about 0.6:1. The preferred degrees of reaction completion in Step 1 are similar to those described above.

The alternative process variants comprise a subsequent third step of working up.

The present invention shows that a significant improvement in phase separation can be achieved when aqueous workup is performed in a temperature range from 50 to 120° C., preferably between 70 and 90° C., whereas the hydrolysis reaction is not yet relevant at the residence times required for the separation. To achieve a sufficient and reproducible product quality (which is a necessary prerequisite for a continuous technical process that must be met), the process of the invention additionally comprises using specific phase separators. At least, a gravitational separator equipped with knits, lamellae or coalescing aids should be used, but a particularly good separation in the alkaline range is achieved by using centrifugal liquid-liquid separators.

The workup of Step 3 comprises both an acidic wash and an alkaline wash, which can likewise be operated in continuous, semicontinuous or batchwise mode, preferably in continuous mode.

Any aqueous acid can be used for the acidic wash, for example HCl, $H_2SO_4$, $H_3PO_4$, $CH_3COOH$. Particular preference is given to aqueous HCl, in particular in a concentration range from 0.5 to 10%. Any conventional basic salt can be used for the alkaline wash, for example NaOH, $Na_2CO_3$, $NaHCO_3$, sodium acetate and corresponding potassium salts. Particular preference is given to Na salts, in particular NaOH in a concentraion range from 0.5 to 10%.

The process of the invention is particularly suitable for continuously preparing bisphenol A diphosphate (BDP) or resorcinol diphosphate (RDP), in which case the polyol used is resorcinol.

The phosphoric acid esters prepared by the methods of the present invention can be utilized as flame retardants in resin compositions. The resin may be a polymer and may include polyphenylene oxide, high-impact polystyrene, polycarbonate, polyurethane, polyvinyl chloride, acrylonitrile-butadiene-styrene, polybutylene terephthalate and mixtures thereof. A wide variety of other polymer resins may also be used.

The examples which follow illustrate the invention. The resulting bisaryl phosphate is characterized with regard to monomer content, acid number, hydrolysable chlorine and magnesium content (catalyst). The characteristic parameters are determined by well-known methods:

The monomer content is determined by liquid chromatography (reverse phase HPLC) using a UV detector at 254 nm.

The acid number is determined by titration with KOH in ethanol.

Residual hydrolyzable chlorine is analysed by hydrolyzing the chlorine attached to phosphorus with sodium methoxide in methanol followed by titration of chloride with silver nitrate.

The magnesium content of the phosphoric acid ester is measured by means of conventional atomic absorption methods.

EXAMPLES

Example 1

Preparation of Bisphenol A Bis(diphenylphosphate)

Experiments were conducted in a tank battery consisting of 4 1 reactors equipped with a stirrer, thermocouple, condenser, and heating mantle. The reaction mixture is kept constant at 1 1 by means of an overflow. The reaction temperature is set separately for each reactor via a separate thermostat.

Stage 1

The reaction mixture ($POCl_3$/BPA mole ratio=5.0, $MgCl_2$ 7 mmol/mol BPA) is introduced into an interchangeable receptacle at 50° C. and transferred to the first reactor by means of a pump. Hydrochloric acid liberated in the reaction is vented and absorbed in water. The following temperature profile is set for the tank battery 82/86/105/120° C. The flow rate is 1.5–2.0 l/h, resulting in an average residence time of 2–2.5 h.

After the reaction, excess $POCl_3$ is continuously distilled off in a falling film evaporator and returned to the reaction. Cl content: 29.4%

Stage 2

The intermediate from Stage 1 is introduced into a receptacle and admixed with the desired amount of phenol at 50° C. (8 mol % excess based on the Cl content of the intermediate). The reaction mixture is transferred to the first reactor by means of a pump. The following temperature profile is set: 135/160/190/210° C. The flow rate is 1.0–1.3 l/h. The average residence time is 3–4 hours.

After the reaction, excess phenol is continuously distilled off in a falling film evaporator and returned to the reaction.

The resulting BDP had the following properties:

Monomer content: 80.5%

Acid number: 1.2 mg KOH/g

Hydrolyzable chlorine: 757 ppm

Mg content: 260 ppm

Example 2

BDP prepared as decribed in Example 1 was used for the workup.

The product was washed with 1% strength HCl and then washed neutral with deionized water, followed by a 2-stage alkaline wash using 2% strength NaOH. Finally, the product was again washed neutral with deionized water and then dried by simple continuous evaporation until a water content of <500 ppm was reached.

Step 3 was carried out as a multistage procedure at 1 bar and at a temperature of 85° C. under a nitrogen blanket.

A feed of 0.9 l/h of the product of Step 2 was subjected to an HCl wash with 1% strength HCl (feed rate 450 ml/h) in Stage 1, a water wash (feed rate 250 ml/h) in Stage 2, an alkaline wash (feed rate 300 ml/h of 2% strength NaOH) in Stages 3 and 4 and a final water wash (feed rate 250 ml/h) in Stages 5 and 6 and finally fed to a centrifuge in Stage 7.

Final drying of the product at 60 mbar and 120° C. gave the desired product which had an Mg content of 30 ppm, an acid number of 0.12 mg KOH/g and a chlorine content of 52 ppm.

The following apparatuses were used in Step 3:

| Stage | Mixer | Phase separation |
|---|---|---|
| Acidic wash | Stirred tank | Gravitational separator equipped with PTFE knit |
| Water wash | Mixing pump | Gravitational separator equipped with PTFE knit |
| Alkaline wash | Stirred tank | Gravitational separator equipped with coalescing aid (5 µ metal fibre) |
| | | Mixing and phase separation in V2 centrifuge from CINC, Nevada, USA |
| Water wash | Stirred tank | Gravitational separator equipped with coalescing aid (5 µ metal fibre) |
| | Stirred tank | Gravitational separator equipped with coalescing aid (5 µ metal fibre) |
| Centrifuge | | Subsequent separation in V2 centrifuge from CINC, Nevada, USA |

Example 3

BDP was prepared as described in Example 1 in a continuous laboratory scale apparatus using $MgCl_2$ catalyst and continuously introduced into the washing step.

Product feed rate in Step 3 0.9 l/h

| Stage 1 | Acidic wash: | Feed rate of 1% strength HCl: 440 ml/h |
|---|---|---|
| Stage 2 | Water wash: | Feed rate: 270 ml/h |
| Stages 3 + 4 | Alkaline wash: | Feed rate of 2% strength NaOH: 300 ml/h |
| Stage 5 | Water wash: | Centrifuge feed rate: 270 ml/h |

Apparatuses in Example 3

| Stage | Mixer | Phase separation |
|---|---|---|
| 1 | Stirred tank | Gravitational separator equipped with PTFE knit |
| 2 | Mixing pump | Gravitational separator equipped with PTFE knit |
| 3 | Stirred tank | Gravitational separator equipped with coalescing aid (5 µ metal fibre) |

Mixing and phase separation in V2 centrifuge from CINC, Nevada, USA

Mixing and phase separation in V2 centrifuge from CINC, Nevada, USA

Dying at 60 mbar and 120° C. yields an optically clear product having an acid number 0.06 mg KOH/g, an Mg content of 18 ppm and a chlorine content of 20 ppm.

What is claimed is:

1. A process for preparing phosphoric acid esters comprising:
   (1) reacting a phosphorus oxyhalide continuously, semi-continuously or batchwise with a polyol to produce a content of at least about 60% monomeric halophosphate intermediate,
   (2) reacting the monomeric halophosphate intermediate continuously, semicontinuously or batchwise with an alcohol to produce the desired phosphoric acid ester, and
   (3) working up the product from Step 2 continuously, semicontinuosly or batchwise in a phase separator at temperatures of 50 to 120° C., wherein the product is worked up in an acidic wash and an alkaline wash.

2. The process according to claim 1, wherein at least one step is carried out continuously.

3. The process according to claim 1, wherein all steps are carried out continuously.

4. The process according to claim 1, wherein reaction of the phosphorus oxyhalide with a polyol is carried out at a temperature ranging from about 50 to about 250° C.

5. The process according to claim 1, wherein reaction of the phosphorus oxyhalide with the polyol is carried out in the presence of a catalyst.

6. The process according to claim 5, wherein the catalyst is a Lewis acid.

7. The process according to claim 6, wherein the Lewis acid is magnesium oxide or magnesium chloride.

8. The process according to claim 1, wherein reaction of the monomeric halophosphate intermediate with an alcohol is carried out continuously.

9. The process according to claim 1, wherein the phosphorus oxyhalide is phosphorus oxychloride.

10. The process according to claim 1, wherein the alcohol is a dihydric alcohol selected from the group consisting of bisphenol A, resorcinol, and mixtures thereof.

11. The process according to claim 1, wherein the alcohol is a monohydric alcohol.

12. The process according to claim 1, wherein the monohydric alcohol is phenol.

13. The process according to claim 1, wherein the monomeric halophosphate intermediate is a diphosphorotetrahalidate.

14. The process according to claim 1, wherein the temperature in Step 3 is between 70 and 90° C.

* * * * *